United States Patent [19]

Anello et al.

[11] 4,340,762

[45] Jul. 20, 1982

[54] GAS PHASE SYNTHESIS OF BIS(TRIFLUOROMETHYL) DISULFIDE

[75] Inventors: Louis G. Anello, Hamburg; Richard F. Sweeney, Elma, both of N.Y.

[73] Assignee: Allied Corporation, Morris Township, Morris County, N.J.

[21] Appl. No.: 216,034

[22] Filed: Dec. 15, 1980

[51] Int. Cl.$^3$ ............................................. C07C 148/00
[52] U.S. Cl. ........................................................ 568/24
[58] Field of Search ......................................... 568/24

[56] References Cited

U.S. PATENT DOCUMENTS 3,790,627  2/1974  Magerlein et al. ..................... 568/24

OTHER PUBLICATIONS

J. V. Martin, J. Chem. Soc., 2944 (1964), Reaction of Fluoro-olefins with Sulfur.
M. Hauptschein et al., J.A.C.S., 73, 5461-63 (1951), Perfluoro-n-propyl Disulfide & Perfluoro-n-propyl Trisulfide.
E. W. Lawless and L. D. Harman, J. Inorg. & Nuclear Chem., 31, 1541 (1969).
C. T. Tullock and D. D. Coffman, J. Org. Chem., 25, 2016 (1960).
R. E. Banks and R. N. Haszeldine, Advances In Inorganic Chem., 3, 414-416 (1961).

Primary Examiner—Mary C. Lee
Attorney, Agent, or Firm—Thomas D. Hoffman; Jay P. Friedenson

[57] ABSTRACT

A method of preparing bis(trifluoromethyl) disulfide, which comprises contacting, in the gaseous state, 2,2,4,4-tetrakis(trifluoromethyl)-1,3-dithietane with activated carbon catalyst at elevated temperature is disclosed.

10 Claims, No Drawings

GAS PHASE SYNTHESIS OF BIS(TRIFLUOROMETHYL) DISULFIDE

BACKGROUND OF THE INVENTION

Field of the Invention

This invention relates to a method of preparing bis(trifluoromethyl) disulfide by contacting, in the gaseous state, 2,2,4,4-tetrakis(trifluoromethyl)-1,3-dithietane with activated carbon at elevated temperature.

Bis(trifluoromethyl) disulfide, a known compound (bp 34° C.), is an intermediate useful for the preparation of compounds containing trifluoromethylthio group, such as the fungicide bis(trifluoromethylthio) mercury.

C. T. Tullock et al. in *J. Org Chem.*, 25, 2016 (1960) disclose preparation of bis(trifluoromethyl) disulfide by liquid phase fluorination of trichloromethyl sulfenylchloride with sodium fluoride at 200°–250° C. in the presence of an organic solvent such as tetramethylene sulfone. R. E. Banks et al. in *Advances in Inorganic Chem.*, 3, 414 (1961) disclose preparation of bis(trifluoromethyl) disulfide by reaction of iodine pentafluoride with carbon disulfide at autogeneous pressures and at temperatures of 200° C., without a solvent. However, these prior art preparations are limited to liquid phase, batch operation which provide commercially unacceptably low conversion of costly reactants and commercially unacceptable low yields of bis(trifluoromethyl) disulfide.

Accordingly, it is an object of the present invention to provide a method for preparing bis(trifluoromethyl) disulfide, in the gas phase without solvent or diluent, from a readily available starting material.

It is a further object of the present invention to provide a continuous method for preparing bis(trifluoromethyl) disulfide, in the gas phase, in the presence of a inexpensive solid catalyst with commercially acceptable yield and commercially acceptable conversion rates of a readily available starting material.

SUMMARY OF THE INVENTION

In accordance with the present invention there is provided a method of preparing bis(trifluoromethyl) disulfide, which comprises contacting, in the gaseous phase, 2,2,4,4-tetrakis(trifluoromethyl)-1,3-dithietane with an activated carbon catalyst at elevated temperature.

DETAILED DESCRIPTION OF THE INVENTION

The present invention provides a one-step method which comprises contacting vaporous 2,2,4,4-tetrakis(trifluoromethyl)-1,3-dithietane with activated carbon, preferably granular activated carbon, at elevated temperature for a time sufficient to produce an effluent stream containing bis(trifluoromethyl) disulfide in commercially acceptable yields, usually in the range of about 8–15 weight percent of the effluent stream. The bis(trifluoromethyl) disulfide can be recovered from the effluent stream comprising $(CF_3)_2C=C(CF_3)_2$, $(CF_3)_2C=CF_2$ and $CF_3SSCF_3$ by condensing the effluent stream under sufficiently high pressure and low temperature to condence the bis(trifluoromethyl) disulfide and recovering bis(trifluoromethyl) disulfide from the condensate by any convenient separation technique such as fractional distillation.

It is a special feature of the present invention that it operates to form bis(trifluoromethyl) disulfide by simply contacting neat, vaporous 2,2,4,4-tetrakis(trifluoromethyl)-1,3-dithietane with granular activated carbon catalyst; no diluent such as a solvent is required to be present and thus no additional separation step is required for recovering bis(trifluoromethyl) disulfide from the effluent stream containing same.

It is a preferred feature of the present invention to use a tubular reactor for the gas phase contact of 2,2,4,4-tetrakis(trifluoromethyl)-1,3-dithietane with granular activated carbon catalyst. The tubular reactor comprises a generally non-porous elongated cylindrical member comprising material that does not interfere with the method of the present reaction and that retains its integrity under the reaction condition. Among the materials found useful for construction of the non-porous cylindrical member are ALUNDUM ® (available from the Norton Company of Worcester, Mass.), nickel, MONEL ®, INCONEL ® or stainless steel.

The activated carbon catalyst used in the present invention can be any type of conventional granular activated carbon prepared from materials such as coal, especially bituminous coal, wood, petroleum, nutshells, coconut shells, and the like. Desirably, the granular activated carbon has a relatively large surface area in the range of about 300–2000 $m^2/g$, preferably about 500–1500 $m^2/g$. Among the granular carbon materials found useful are activated carbons available from standard commercial sources, such as Columbia MBV, Columbia JXC, Columbia SBV and Darco. The granular size of the granular activated carbon catalyst employed is not critical. When the method of the present invention is preferably carried out in an elongated non-porous tubular reactor, it is convenient to employ granular activated carbon catalyst having an average mesh size in the range of about 1/25 to ¼ of the inside diameter of the tubular reactor. Granular activated carbon catalyst having an average mesh size in the range of about ⅛ to 1/10 of the inside diameter of the tubular reactor, thereby permitting the volume of said tubular reactor to be substantially occupied by said catalyst, is preferred.

The elevated temperatures employed in the reaction are generally between about 250° C. and about 500° C., preferably between about 350° C. and about 450° C., and more preferably between about 375° C. and about 425° C.

The present invention is conveniently carried out at atmospheric pressures; super-, and sub-atmospheric pressures may be employed without affecting the results achieved at atmospheric pressure.

The contact time for the method of the present invention is not critical. Appreciable conversions of 2,2,4,4-tetrakis(trifluoromethyl)-1,3-dithietane vapor are observed even at a contact time as short as about 0.5 seconds. Commercially acceptable yields of bis(trifluoromethyl) disulfide, in the range of about 8 to about 15 weight percent of the effluent stream, are achieved when the contact time is in the range of about 25–60 seconds. Generally, contact times can be varied from about 0.5 seconds to about 5 minutes, preferably about 1 second to about 60 seconds, more preferably about 25–60 seconds.

The 2,2,4,4-tetrakis(trifluoromethyl)-1,3-dithietane,

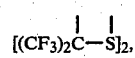

used in the present invention is readily prepared in high yield by reaction of hexafluoropropylene with sulfur over activated carbon at elevated temperatures (J. V. Martin, *J. Chem. Soc.* 2944 (1964)).

While the method of the present invention includes both batch and continuous operation, it is a special feature of the present invention that continuous operation is conveniently employed in standard equipment by continuously passing vaporous 2,2,4,4-tetrakis(trifluoromethyl)-1,3-dithietane over activated carbon catalyst at elevated temperatures and continuously recovering bis(trifluoromethyl) disulfide from the effluent stream.

The following examples illustrate and describe the present invention. However, the scope of the present invention is to be interpreted only in view of the appended claims.

EXAMPLE I

One hundred forty-five mL of Columbia JXC activated carbon (4–6 mesh) were charged to a 1" (2.54 cm) I.D. MONEL ® tubular reactor, 27" long (68.6 cm), heated externally over about 24" (61.0 cm) of its length by an electric furnace provided with automatic temperature control. During a period of four hours, 478 g (1.31 M) of

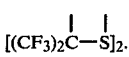

were passed over the catalyst at a reaction temperature of 425° C. and a contact time of about 25 seconds. Exit products from the reactor were passed into a dry ice-acetone cooled trap. Fractional distillation of the cold trap product, 441 g, effected recovery of 24.3 g (0.12 M, 15.4% yield) of $(CF_3)_2C=CF_2$; 14.5 g (0.071 M, 9% yield) of desired $CF_3SSCF_3$; 86 g (0.31 M, 39.1% yield) of $(CF_3)_2C=C(CF_3)_2$ and 191.3 g (0.52 M) of unreacted

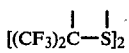

Thus, of the starting material fed, 5.4% was converted to $CF_3SSCF_3$.

EXAMPLE II

Following the procedure of Example I, 411 g (1.11 M) of

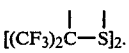

was passed over the above carbon catalyst during a period of 4 hours at a reaction temperature of 450° C. and a contact time of about 26 seconds. Fractional distillation of the cold trap product, 372.4 g, effected recovery of 33.5 g. (0.17 M, 19.2% yield) of $(CF_3)_2C=CF_2$; 26 g (0.13 M, 15% yield) of desired $CF_3SSCF_3$; 66 g (0.22 M, 25.2% yield) of $(CF_3)_2C=C(CF_3)_2$ and 87 g (0.24 M) of unreacted

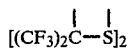

The conversion to $CF_3SSCF_3$ was 11.7% based on starting material fed.

EXAMPLE III

Following the procedure of Example I, 343 g (0.94 M) of

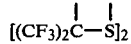

was passed over 145 mL of Columbia MBV carbon at a reaction temperature of 425° C. and a contact time of about 25 seconds. Fractional distillation of the cold trap product, 324.5 g, effected recovery of 9.7 g (0.05 M, 7.6% yield) of $(CF_3)_2C=CF_2$; 12.3 g (0.06 M, 9.6% yield) of desired $CF_3SSCF_3$; 715 g (0.24 M, 38% yield) of $(CF_3)_2C=C(CF_3)_2$ and 111 g (0.13 M) of unreacted

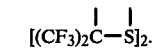

The conversion to $CF_3SSCF_3$ was 6.4% based on starting material fed.

EXAMPLE IV

Following the procedure of Example I, 346 g (0.95 M) of

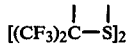

was passed over 145 mL of Columbia SBV carbon during a period of 3 hours at a reaction temperature of 425° C. and a contact time of 25 seconds. Fractional distillation of the cold trap products effected recovery of 16.3 g (0.08 M, 11% yield) of $(CF_3)_2C=CF_2$; 12 g (0.06 M, 8% yield) of desired $CF_3SSCF_3$; 84.2 g (0.28 M, 38,3% yield) of $(CF_3)_2C=C(CF_3)_2$ and 80 g (0.22 M) of unreacted

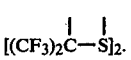

The conversion to $CF_3SSCF_3$ was 6.3% based on starting material fed.

We claim:

1. A method for preparing bis-(trifluoromethyl) disulfide, which consists essentially of contacting, in the gaseous phase, 2,2,4,4-tetrakis(trifluoromethyl)-1,3-dithietane with an activated carbon catalyst at elevated temperature, producing an effluent stream comprising bis(trifluoromethyl) disulfide and recovering bis(trifluoromethyl) disulfide from the effluent stream.

2. The method of claim 1 wherein the temperature is between about 250° C. and about 500° C.

3. The method of claim 1 wherein the temperature is between about 350° C. and about 450° C.

4. The method of claim 1 wherein the temperature is between about 375° C. and about 425° C.

5. The method of claim 1 wherein the recovering step comprises condensing said effluent stream under sufficiently high pressure and low temperature to condense bis(trifluoromethyl) disulfide.

6. The method of claim 1 wherein granular activated carbon catalyst is disposed in a non-porous tubular reactor.

7. The method of claim 6 wherein the granular activated carbon catalyst is of an average mesh size in a range of about 1/25 to about ¼ of the inside diameter of said tubular reactor.

8. The method of claim 7 wherein said average mesh size is in the range of about ⅛ to about 1/10 of the inside diameter of said tubular reactor.

9. The method of claim 1 or 6 wherein the contacting step comprises continuously passing, in the gaseous phase, said dithietane over an activated carbon catalyst.

10. The method of claim 7 or 8 wherein the surface area of the granular activated carbon catalyst is in the range of about 500 to 1500 $m^2/g$.

* * * * *